United States Patent [19]

Crossley

[11] Patent Number: 4,831,887
[45] Date of Patent: May 23, 1989

[54] AUTOMATIC SAMPLING MACHINE

[75] Inventor: Alan M. Crossley, Surrey, Great Britain

[73] Assignee: Thames Water Authority, United Kingdom

[21] Appl. No.: 3,278

[22] Filed: Jan. 14, 1987

[30] Foreign Application Priority Data

Jan. 14, 1986 [GB] United Kingdom ............... 8600780

[51] Int. Cl.$^4$ ............................................. G01N 1/14
[52] U.S. Cl. ................................................. 73/864.34
[58] Field of Search ........... 73/863.01, 863.83, 863.84, 73/864.34, 864.35

[56] References Cited

U.S. PATENT DOCUMENTS

| | | | |
|---|---|---|---|
| 3,039,309 | 6/1962 | Vesper et al. | 73/863.83 |
| 3,795,347 | 3/1974 | Singer | 73/864.35 |
| 3,924,471 | 12/1975 | Singer | 73/864.35 |
| 4,023,417 | 5/1977 | McClure | 73/864.35 |
| 4,037,472 | 7/1977 | Gates | 73/864.35 |
| 4,418,581 | 12/1983 | Jones | 73/864.34 |
| 4,604,166 | 8/1986 | Weinberg et al. | 73/864.34 |

*Primary Examiner*—Stewart J. Levy
*Assistant Examiner*—Robert R. Raevis
*Attorney, Agent, or Firm*—Larson & Taylor

[57] ABSTRACT

A device for automatically sampling liquids includes a reversible gas powered motor driving a reversible pump. There are included in lines supplying the driving gas to the motor control devices which cause the gas to drive the motor and the pump in one sense for a predetermined period of time to purge the pump and subsequently to drive the motor and the pump in the opposite sense to draw a sample of the liquid. The motor preferably has two inputs. During the initial period of time the driving gas is connected to the first input driving the pump in the first sense. Subsequently the control devices remove the supply from the first input and connect it to the second input driving the pump in the opposite sense for a predetermined period of time and then stopping the motor. The control device is then reset so that upon the following actuation of the motor it is driven again in the one sense. The control devices include a purge timer, a sample timer, and two bistable devices, one bistable device being associated with each timer. These are in turn linked to a time-counter which controls the interval between successive pairs of purging and sampling operations.

1 Claim, 3 Drawing Sheets

AUTOMATIC SAMPLING MACHINE

BACKGROUND OF THE INVENTION

The present invention concerns the design and method of operation of a device for taking samples from sources of liquid such as, bore holes, sumps, conduits carrying liquid chemicals such as petroleum or alcohols, a stream of water, sewers or effluent channels. It is particularly concerned with the provision of a machine to be used in environments which, by virtue of a susceptibility to flooding or the presence of noxious or flammable gases, are hostile.

Sampling methods known at their simplest include manually taking a sample using a scoop or other such device. Clearly requiring the person sampling either to make repeated returns to the sample point or to remain at the sample point over an extended period of time is both an inefficient use of manpower and, in a hostile environment such as a sewer, potentially dangerous. To overcome this disadvantage a sampling machine capable of operating unattended is desirable. In realising this objective a number of difficulties are to be overcome. When a multiplicity of sites are to be covered but samples are required only infrequently at any given site it is uneconomic to build fixed installations: the sampling machine must therefore be capable of being portable. For the sampling machine to be taken to sites where access is difficult the machine must be compact and rugged.

The major difficulty is the requirement that the machine must be able to operate safely in the presence of liquids and/or potentially explosive gases. Electrically operated systems would have to be comprehensively insulated and isolated from their immediate environment to operate safely. Attaining this degree of insulation and isolation adds significantly to the cost of the device and makes it more difficult to obtain the goals of compactness and portability. In many situations the provision of a supply of electricity is difficult if not impossible. In addition to meeting these requirements the sampling machine must efficiently fulfill its prime purpose of drawing a series of samples over a period of time. To provide valid results it is desirable that each sample is discrete, i.e. that each sample is not contaminated with residues from any preceding sample.

One past attempt at solving the problems addressed by the present invention is disclosed in FR No. 2343239. This machine is an electro-mechanical device having a reversible peristaltic pump driven by a conventional electric motor an, in the principal embodiment, a rotatable delivery tube driven by an electronically controlled stepper motor. In use the liquid drawn by the pump is transferred to the delivery tube and then to one of a number of fixed containers. Since, unlike the system of the present invention, this machine relies upon electricity for motive power and control it is inherently ill-adapted for use in hazardous areas. It is attempted to overcome this problem by sealing the electric motor within a plastic compartment. Since it is necessary for the device's control panel to be accessible this cannot be positioned within the sealed compartment and so each of the switches on the control panel has to be individually sealed. Sealing all the electrical components to the high standards necessary for safe use in the presence of liquids and flammable gases necessarily adds significantly to the cost of manufacture and maintenance of the device and the need to have particular components positioned within sealed compartments contains the layout of the components within the device, limiting the extent to which its overall volume can be reduced.

The sampling machine disclosed in FR No. 2343239 has further major disadvantages in that complete purging of the sampling/delivery system is not possible. Reversing the direction of the peristaltic pump serves to purge the tubes directly connected to the pump but leaves the rotatable delivery tube unpurged. Any residues in the form of liquids or liquid-borne solids within the delivery tube will therefore tend to contaminate subsequent samples.

Another electrically, powered sampling device is disclosed in U.S. Pat. No. 3,795,347. This device uses a two-stage sampling process in which liquid is drawn under vacuum into a closed metering chamber until it rises to a predetermined level within the chamber and then the entire contents of the chamber are expelled under pressure into a storage vessel. Prior to a sample being drawn into the metering chamber pressure is applied to purge residues from the chamber and from a tube linking the source of liquid to the chamber. The device uses an electrically powered pump to pressurise the metering chamber and electrically powered timing and control devices. It therefore suffers all the attendent disadvantages discussed above in relation to FR No. 2343239. Moreover it is impossible for this device to be comprehensively insulated since it relies upon a pair of electrodes being exposed to the sample fluids in the metering chamber. It is therefore not possible to operate this device with complete safety in electrically hazardous environments. The two stage sampling process makes this device operationally less efficient than a device in accordance with the present invention in which the pump acts directly upon the liquids to draw a sample rather than being used indirectly to pressurise or evacuate an intermediate chamber. Since the process of purging can never be totally effective, particularly when liquid-borne solids are present, the use of an intermediate chamber provides an additional source of contamination of samples. Furthermore the tube leading from the metering chamber to the vessel for retaining the sample is not purged by the initial pressurisation of the chamber and so provides a further source of contamination. In all these respects this device contrasts with the present invention which provides a direct and easily purged connection between the source of the liquid and the outputs of the device.

SUMMARY OF THE INVENTION

According to the present invention a device for automatically sampling liquids includes a reversible gas powered motor driving a reversible pump and control means associated with lines supplying a driving gas to the motor, the control means being arranged to supply the driving gas to the motor to drive it and the pump in one sense for a predetermined period of time to purge the pump and then to supply the driving gas to the motor to drive it and the pump in the opposite sense to draw a sample of the liquid.

Preferably the gas powered motor has two inputs and the change in direction of the motor is achieved by the control means connecting the supply of the driving gas to a first input during the initial period of time then connecting the supply to a second input.

Preferably the control means is arranged to draw a sample of predetermined volume by driving the motor in the opposite sense for a predetermined period of time and then stopping the motor. The control means then resets so that upon the following actuation of the motor it is driven in the one sense. Preferably the control means includes a purge timer and a sample timer, and two bistable devices, one bistable device being associated with each timer. Preferably these timers and bistable devices are in turn linked to a further timer, an interval timer to control the interval between successive pairs of purging and sampling operations.

In a preferred method of operation of a device in accordance with the present invention the sampling sequence is initiated by starting the interval timer which determines the delay before purging and sampling operations. When the period set on the interval timer has elapsed a signal to initiate a first mode of operation is sent to the purge timer and its associated bistable device, causing the gas supply to the first input of the motor to be turned ON, so driving the motor and the pump in one sense to discharge any residue from a previous sample. After the time set on the purging timer has elapsed a signal is sent to its associated bistable device, to the sample timer and to that timer's associated bistable device, turning OFF the driving gas supply to the first input of the motor, turning ON the driving gas supply to the second input of the motor and starting the sample timer. This causes the motor and pump to operate in their opposite sense and draw a sample. When the period set on the sample timer elapses that timer sends a signal to its associated bistable device, turning OFF the driving gas supply to the second input of the motor and hence removing power from the motor. Switching means connected to the supply lines for the first and second motor inputs and logically equivalent to a NOT gate then sense that both bistable devices are in the OFF position and send a signal to the interval timer resetting it to its original condition and initiating a repetition of the above operational sequence.

In an alternative method of operation the control system is so arranged that in a first mode of operation the pump is driven in a sense such that a sample is drawn and then in a second mode of operation the pump is driven in the opposite sense purging any sample residue.

Preferably the motor is powered by a compressed gas such as air, and preferably the pump is a totally enclosed peristaltic pump. Preferably the control system includes at least one manually operable pneumatic switch to produce a signal to draw a single sample.

The device may include a turntable or other movable device on which a number of containers for samples are mounted and means to cause the turntable or other movable device to advance to align a fresh container with the outlet of the pump. The control means may enable each container to remain stationary for a preset number of sampling/purging cycles so that the sample represents a time averaged state of the sampled liquid over an extended period or alternatively a fresh container may be used for each sampling/purging cycle.

The timer may comprise a continuous extended period timer, however the interval timer preferably comprises a short period timer and an associated batch counter, the batch counter producing a pneumatic signal when the short period timer has gone through a pre-set number of cycles.

The control system may include a delay timer to enable the apparatus to be pre-set to perform a sampling sequence or sequences at a time or times separated from the occasion of the initial setting of the device by a period of, for example, several hours or several weeks.

BRIEF DESCRIPTION OF THE DRAWINGS

A device in accordance with the present invention and its method of operation will now be described with reference to the accompanying drawings; in which.

DESCRIPTION OF THE DRAWINGS

Figure 1:
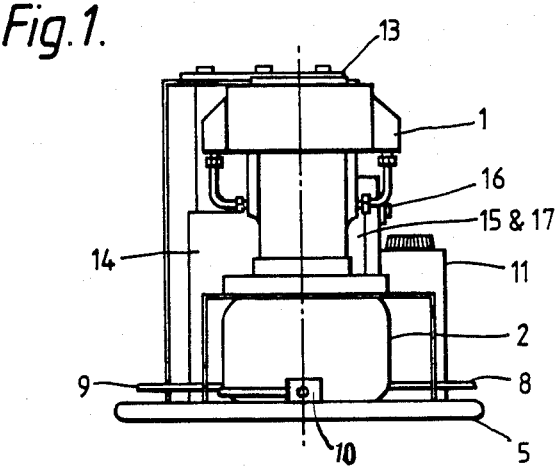
FIG. 1 is a side elevation.

A compressed air driven motor 1, a peristaltic pump 2 and a pneumatic control system 3 mounted on a connecting block 4 are all mounted on a base plate 5. Two supply lines 6 and 7 link the motor 1 to the control system 3. The pump 2 includes an inlet 8 and an outlet 9 for the sampled liquid. An air inlet 10 is connected to the pneumatic control system.

The motor 1 is preferably of the type commercially available as DYNATORK 1 from Kinmore Engineering Limited, a low working volume motor enabling the device to operate continuously from a single cannister of compressed air for periods of at least as long as twenty-four hours. It is mechanically coupled to the adjacent peristaltic pump 2 which is the type commercially available as model no. 303 from Watson & Marlow Ltd. A line connected to the pump inlet 8 links the pump 2 to the source of the sampled liquid. A line connected to the pump outlet 9 carries the sampled liquid to a container (not shown) in which it is to be collected.

Figure 4:
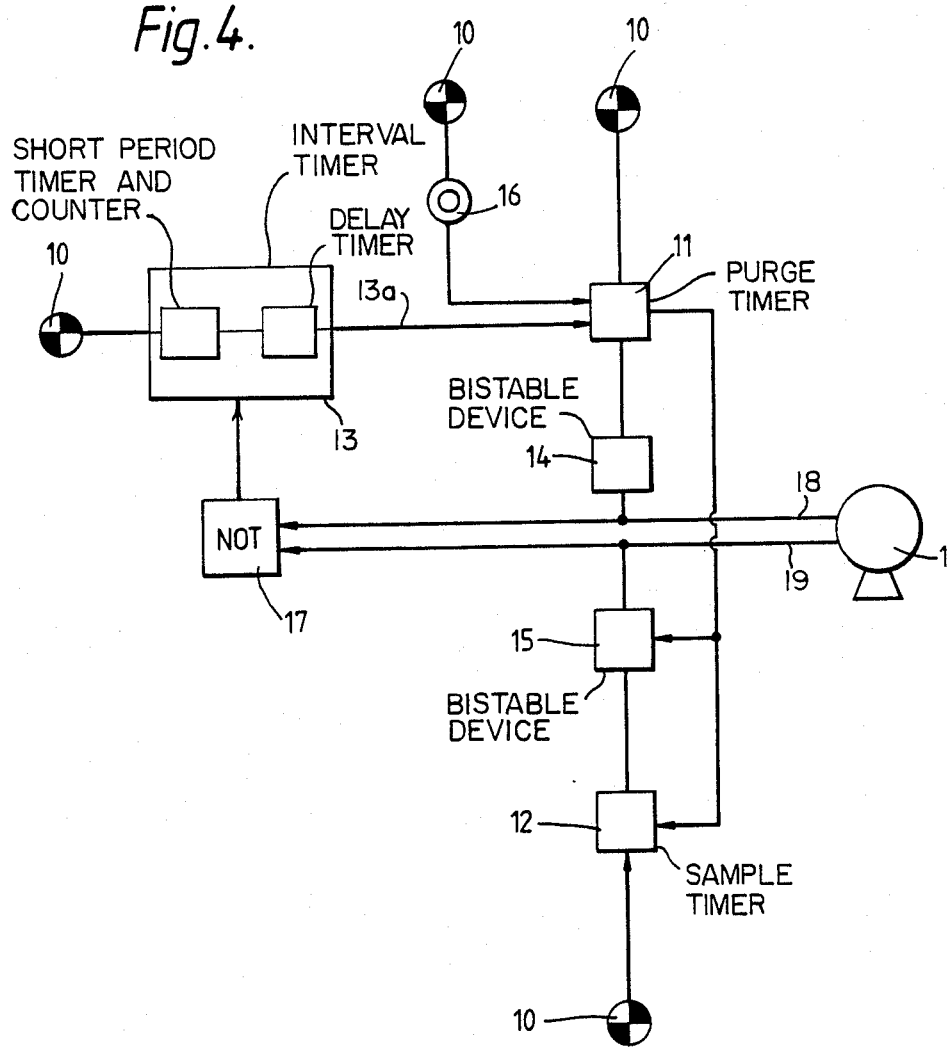
FIG. 4 is a pneumatic circuit diagram.

The control system 3 is shown in detail in FIG. 4 and includes three adjustable pneumatic timers, an interval timer 13, comprising a short period timer and an associated batch counter, purge timer 11 and a sample timer 12. The control system further includes two fluidic bistable devices, 14 and 15, one associated with the purge timer 11 and the other associated with the sample timer 12, a manually operable switch 16 and a fluidic NOT gate 17. The time period set on the sample timer 12 is smaller than that of the purge timer 11 which is in turn smaller than that of the interval timer 13.

Figure 2:
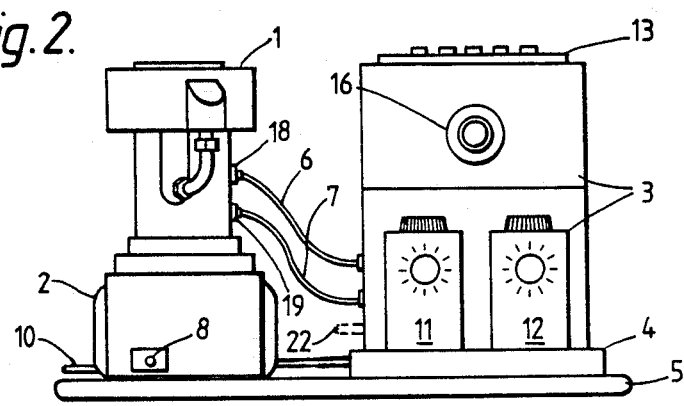
FIG. 2 is a front elevation.
Figure 3:
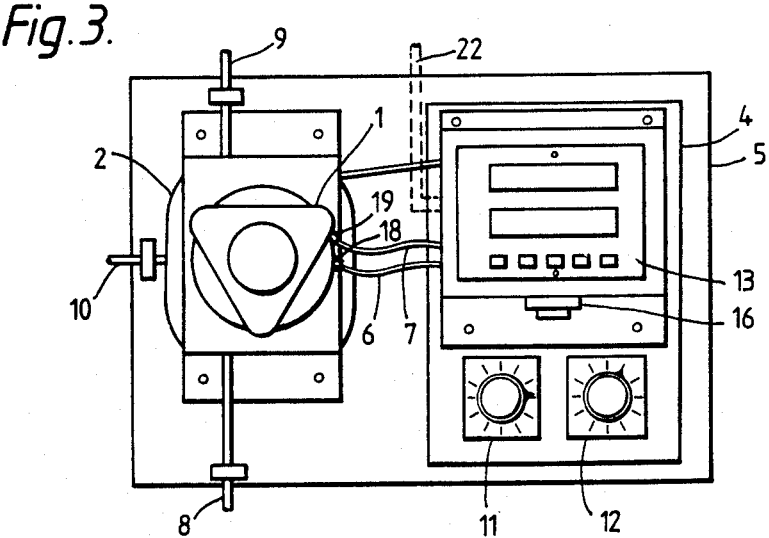
FIG. 3 is a plan.

To initiate a sampling sequence compressed air is admitted to the main air inlet 10 and this starts the timing period of the interval timer 13. When the time preset on the interval timer 13 has expired a pneumatic signal is produced and transmitted via airways in the connecting block 4 (represented at 13a in FIG. 4) to the purge timer 11 and its associated fluid bistable device 14. This fluidic bistable device 14 admits air from the air inlet 10 to a first input 18 of the motor 1, driving the motor 1 and hence the pump 2 in a first sense such that the pump 2 it draws air from the atmosphere and pumps it through the line connected to the sample inlet 8 (FIGS 1 to 3) so purging the residue of any previous liquid sample.

At the expiry of the time period of the purge timer 11 it outputs a pneumatic signal which switches off its associated bistable device 14, switches on the sample timer 12 and switches on that timer's associated bistable device 15. Air is admitted through this bistable device 15 to a second input 19 of the motor 1 driving the motor 1 and hence the pump 2 in the opposite sense such that it draws a sample of liquid from the source through the line connected to the inlet 8 of the pump 2 and feeds it to the container (not shown) where it is retained. When the time period set by sample timer 12 expires it outputs a pneumatic signal which switches off its associated bistable device 15 cutting off the air supply to the motor 1. In response to the condition in which both bistable devices 14, 15 are OFF the NOT gate 17 produces a pneumatic signal which resets the interval timer 13 and initiates a new sampling cycle.

Figure 5:
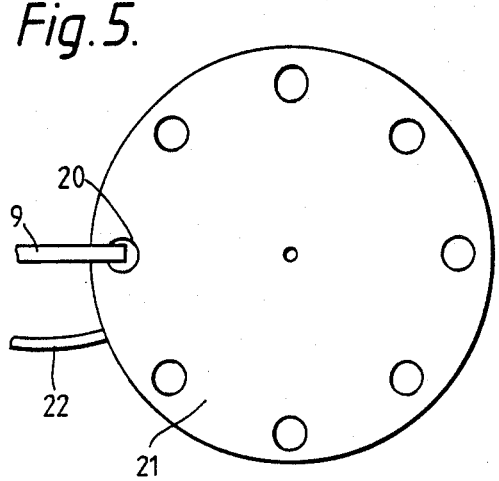
FIG. 5 is a plan of a turntable; and,
FIG. 6 is a partially sectional side elevation of a turntable.
Figure 6:
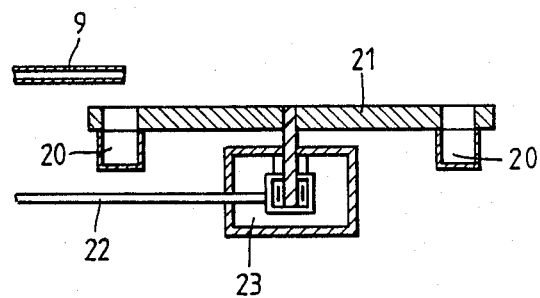

As shown in FIGS. 5 and 6, the pump outlet 9 may deliver the sampled liquid to a container 20 mounted on the periphery of a turntable 21. In this embodiment the device includes a line 22 (shown dashed) linking the control system 3 to a pneumatic motor 23 arranged to index the turntable bringing a fresh container 20 to the outlet 9 after each complete sampling cycle.

In alternative method of operation the manually operable switch 16 is operated to transmit a signal to the purge timer and to its associated fluidic bistable device 14 to initiate a single cycle in which the pump 2 is purged and then a single sample is drawn.

I claim:

1. A method for operating a device for automatically sampling a liquid or liquids, said device comprising: a reversible gas powered motor having first and second inputs; a reversible peristaltic pump driven by said motor; at least two supply lines connected to said first and second inputs of said motor for supplying a driving gas to said motor; control means connected to said supply lines for causing gas to be supplied to said motor to drive said motor and said pump in a first direction for a first predetermined period of time to purge said pump and for then causing said gas to be supplied to said motor to drive said motor and said pump in the opposite direction to said first direction to draw a sample of said liquid, said control means including a purge timer, a sample timer, a first bistable device connected to said purge timer, a second bistable device connected to said sample timer, and an interval timer to which said purge timer, said sample timer and said bistable device being connected so that said interval timer controls the interval between successive pairs of purging and sampling operations; and device further comprising a fluidic NOT gate connected to said at least two supply lines and to said interval timer, said fluidic NOT gate being adapted to transmit a pneumatic signal to said interval timer upon sensing that the supply of gas to said first and second inputs is off, thereby resetting said interval timer, said method comprising:

initiating said interval timer; when the period set by said interval timer has elapsed, sending a signal to initiate a first mode of operation to said purge timer and said first bistable device causing the gas supply to said first input of said motor to be turned on, so driving said motor and said pump in said one direction to discharge any residue from a previous sample; after the time set by said purge timer has elapsed, sending a signal to said fist bistable device, to said sample timer and to said second bistable device, so as to turn off the driving gas supply to said first input of said motor, to turn on said driving gas supply to said second input of the motor thereby causing said motor and said pump to operate in said opposite direction and draw a sample, and to start said sample timer; when the period set by said sample timer has elapsed, sending a signal to said second bistable device, so as to turn off the driving gas supply to the second input of said motor and to hence remove power from said motor; and sensing when both said first and second bistable devices are in the off state thereof and sending a signal to said interval timer to initiate a repetition of the operational sequences.

* * * * *